United States Patent
Henderson

(10) Patent No.: US 9,089,432 B1
(45) Date of Patent: Jul. 28, 2015

(54) INJECTABLE HIP HEMIARTHROPLASTY

(71) Applicant: Eric Ross Henderson, Boston, MA (US)

(72) Inventor: Eric Ross Henderson, Boston, MA (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/218,305

(22) Filed: Mar. 18, 2014

Related U.S. Application Data

(62) Division of application No. 13/349,264, filed on Jan. 12, 2012, now Pat. No. 8,715,365.

(60) Provisional application No. 61/431,933, filed on Jan. 12, 2011.

(51) Int. Cl.
    *A61F 2/36* (2006.01)

(52) U.S. Cl.
    CPC ............. *A61F 2/3601* (2013.01); *A61F 2/36* (2013.01); *A61F 2/3662* (2013.01); *A61F 2002/365* (2013.01)

(58) Field of Classification Search
    CPC ... A61F 2/36; A61F 2002/365; A61F 2/3662; A61F 2220/0033
    USPC ............................................ 623/23.11, 23.46
    See application file for complete search history.

(56) References Cited

U.S. PATENT DOCUMENTS

| | | | |
|---|---|---|---|
| 5,147,299 A * | 9/1992 | Mendoza et al. | 600/35 |
| 5,171,289 A | 12/1992 | Tornier | |
| 5,468,245 A | 11/1995 | Vargas, III | |
| 7,044,977 B2 | 5/2006 | Ferree | |
| 2003/0220698 A1 * | 11/2003 | Mears et al. | 623/22.4 |
| 2004/0073308 A1 | 4/2004 | Kuslich et al. | |
| 2005/0171548 A1 | 8/2005 | Kelman | |
| 2006/0264965 A1 | 11/2006 | Shadduck et al. | |
| 2008/0249580 A1 | 10/2008 | Evans et al. | |
| 2008/0312749 A1 * | 12/2008 | May et al. | 623/23.35 |
| 2009/0043344 A1 * | 2/2009 | Schlotterback | 606/86 R |
| 2009/0076517 A1 | 3/2009 | Reiley et al. | |
| 2010/0076481 A1 | 3/2010 | Stephens et al. | |
| 2010/0228355 A1 * | 9/2010 | Linares | 623/22.15 |
| 2010/0266979 A1 * | 10/2010 | Karmon | 433/80 |
| 2012/0123337 A1 * | 5/2012 | Forsell | 604/151 |

FOREIGN PATENT DOCUMENTS

WO          9956674 A1     11/1999

OTHER PUBLICATIONS

Huo et al., What's New in Hip Arthroplasty. J. Bone Joint Surg. Am. 2005. vol. 87 (No. 9): 2133-2146.

* cited by examiner

*Primary Examiner* — Bruce E Snow
*Assistant Examiner* — Melissa Hoban
(74) *Attorney, Agent, or Firm* — Nilay J. Choksi; Smith & Hopen, P.A.

(57) ABSTRACT

The invention discloses a surgical technique and apparatus for minimally invasive replacement of a fractured femoral head in hip arthroscopy. The fractured femoral head is first removed from the patient, and an incision made on the patient on a lateral aspect of the operative thigh. A hole is then drilled into the cortex of the operative femur of the patient through the incision. The femoral neck and femoral canal of the operative femur are reamed by inserting a reamer through the drilled hole. A hip prosthesis is then inserted into the wound and injected with molding. The hip prosthesis includes a femoral component having a distal end and a proximal end, the distal end inserted and anchored in the reamed femoral canal, and a femoral head component with smooth surface. The femoral head component contains a deflated balloon that, when inflated with molding, is similar to a neo-femoral head.

17 Claims, 15 Drawing Sheets

INJECTABLE HIP HEMIARTHROPLASTY

CROSS-REFERENCE TO RELATED APPLICATIONS

This application is a divisional of and claims priority to U.S. Nonprovisional application Ser. No. 13/349,264, entitled "Injectable Hip Hemiarthroplasty", filed Jan. 12, 2012 by the same inventor, which claims priority to U.S. Provisional Application No. 61/431,933, entitled "Injectable Hip Hemiarthroplasty", filed on Jan. 12, 2011 by the same inventor, both of which are incorporated herein by reference in their entireties.

BACKGROUND OF THE INVENTION

1. Field of the Invention

This invention relates, generally, to hip surgery. More particularly, it relates to a surgical technique for hemiarthroplasty that is minimally invasive and has reduced post-operative pain.

2. Description of the Prior Art

Approximately 300,000 patients experience a fracture of the hip due to osteoporosis every year. These patients are generally elderly and often have multiple pre-existing medical conditions, making them poor candidates for a surgical procedure.

Current treatments for hip fracture include total hip arthroplasty (replacement of the femoral and acetabular sides of the hip joint), hip hemiarthroplasty (replacement of the fractured femoral side of the hip only, leaving the native acetabulum in place), and hip pinning with cannulated screws. Occasionally a hip fracture will warrant a hip disarticulation.

The type of treatment for hip fracture is decided by factors such as the patient's pre-fracture level of activity, the existence of pre-existing arthritis, and the patient's health and ability to tolerate surgery. Younger patients who are active are often candidates for hip pinning, so that their native femur may be saved. For patients who are ambulatory and have arthritis, total hip arthroplasty is typically performed. For patients who are ambulatory and do not have arthritis, hip hemiarthroplasty is typically performed. Though less common, hip pinning may be chosen for elderly patients who are not ambulatory if they are judged to be poor surgical candidates and require a less invasive procedure.

International Patent Application No. PCT/US99/08906 discloses a surgical technique of removing the fractured femoral head from a body and inserting a neo-femoral head joined to the native femoral neck. The neo-femoral head comprises a bio-absorbable expandable balloon that is filled with a molding material within the body and forms the shape of the neo-femoral head.

However, several issues arise in this conventional technology. First, the device is made of a bio-absorbable material that will disintegrate over time. The intent of the procedure is for the patient to undergo 6-8 weeks of post-operative crutch-walking, during which time bone will replace the inserted material. Based on known rates of creeping substitution, the process by which bone incorporates bone-line materials may take 10-20 years, prior to which the device would likely fail. Moreover, the neo-femoral head is supported only by a thin cylindrical stem through the femoral neck, thus being susceptible to cantilever bending forces.

Accordingly, what is needed is a rigid, minimally invasive, immediately weight-bearing surgical procedure and apparatus for performing hip hemiarthroplasty. However, in view of the art considered as a whole at the time the present invention was made, it was not obvious to those of ordinary skill how the art could be advanced.

While certain aspects of conventional technologies have been discussed to facilitate disclosure of the invention. Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for a minimally invasive, immediately weight-bearing method and apparatus for replacing the fractured femoral side of the hip is now met by a new, useful and nonobvious invention.

The disclosed invention is a novel surgical technique for minimally invasive replacement of a hip hemiarthroplasty which requires the use of commercially available instruments for hip arthroscopy and a new type of balloon hip hemiarthroplasty component that requires injection of bone cement.

People who may need this novel surgical technique include patients with hip fractures who are limited in their walking capacity or are not candidates for a more invasive procedure, such as hip hemiarthroplasty with a metallic prosthesis. The increasing number of elderly patients would benefit from a less invasive procedure that brings pain relief similar to a hip hemiarthroplasty.

The invention discloses a surgical technique for minimally invasive replacement of a femoral head in hip arthroscopy. The steps comprise placing a patient with fractured hip, containing a fractured femoral head and a femoral neck, in a supine position suitable for the surgical technique. The fractured femoral head is then removed from the patient, and an incision is made on the patient on a lateral aspect of the operative thigh. A hole is then drilled into the cortex of the operative femur of the patient through the incision. The femoral canal of the operative femur can be reamed by inserting a reamer through the drilled hole. The reamer has a flexible shaft and is disposed within a lumen of a trajectory guidance tube. The surgical technique continues by inserting a hip prosthesis into the wound. The hip prosthesis contains a femoral component attached to a deflated balloon with smooth surface. The hip prosthesis can then be injected with a molding, such that the deflated balloon becomes inflated and similar to a neo-femoral head.

In an embodiment, when the patient is placed in the supine position, the operative leg of the patient can be internally rotated by about 15°, so the surgeon can orient surgical instruments parallel to a landmark to achieve correct orientation to the femoral neck.

In an embodiment, the step of removing the fractured femoral head from the patient can be performed using a camera, a grasper, or a bone burr.

In an embodiment, the drilled hole is about 15 mm in diameter to about 20 mm in diameter.

In an embodiment, the trajectory guidance tube contains a 90° elbow to direct the reamer down the length of the femoral canal.

In an embodiment, the molding is bone cement.

In an embodiment, the deflated balloon can be inflated with water or air prior to inflating the deflated balloon with the molding.

In an embodiment, the hip prosthesis includes an external sleeve containing a flexible rod to guide the hip prosthesis into correct position within the subject. The external sleeve is disposed adjacent to the femoral component. In a further embodiment, the external sleeve is collapsible.

In an embodiment, the hip prosthesis includes a insertion sleeve surrounding the deflated balloon. In a further embodiment, the hip prosthesis further includes a guiding string attached to the insertion sleeve. A force can be applied to the guiding string to guide the hip prosthesis into the correct position within the patient. In a further embodiment, the insertion sleeve includes a tab that is pulled to detach the insertion sleeve from the hip prosthesis, so the insertion sleeve can be removed from the patient.

In an embodiment, insertion of the hip prosthesis into the patient can be facilitated by rolling the hip prosthesis into a slimmer form prior to insertion into the patient.

In an embodiment, each component of the surgical technique can be monitored with fluoroscopy while the surgical technique is being performed.

In a separate embodiment, the invention discloses a surgical technique for minimally invasive replacement of a femoral head in hip arthroscopy. The steps comprise placing a patient with fractured hip, containing a fractured femoral head and a femoral neck, in a supine position. The patient is positioned with operative leg internally rotated by about 15°, so a surgeon can orient surgical instruments parallel to a landmark to achieve correct orientation to the femoral neck. The surgeon then removed the fractured femoral head from the patient by using a camera, a grasper, or a bone burr. The surgeon then makes an incision on a lateral aspect of an operative thigh of the subject, so the incision is coincident to a line drawing through a path of the femoral neck. The surgeon then drills a hole into the cortex of the operative femur of the patient through the incision. The hole is about 15 mm in diameter to about 20 mm in diameter. The surgeon then reams the femoral canal of the operative femur by inserting a reamer through the drilled hole. The reamer has a flexible shaft and is disposed within a lumen of a trajectory guidance tube containing a 90° elbow. The region of the fractured hip is then irrigated with a pulse-lavage device. A hip prosthesis is rolled into a slimmer form to facilitate insertion into the patient. The hip prosthesis contains a deflated balloon with smooth surface, a insertion sleeve surrounding the deflated balloon, a femoral component inserted into a femoral canal, a collapsible external sleeve containing a flexible rod to guide the hip prosthesis into correct position within the patient, wherein the external sleeve is adjacent to the femoral component, a guiding string attached to the insertion sleeve, and a tab that is pulled to detach the insertion sleeve from the hip prosthesis, so the insertion sleeve can be removed from the patient. The hip prosthesis can then be inserted into the wound through the incision by inserting the distal end of the femoral component first, followed by the remainder of the hip prosthesis. The deflated balloon is then inflated with water or air and finally then inflated with bone cement, so the deflated balloon becomes inflated and similar to a neo-femoral head.

In a separate embodiment, the invention discloses a hip hemiarthroplasty device, comprising a femoral component having a distal end and a proximal end, the distal end inserted and anchored in the operative reamed femoral canal in the patient, and a femoral head component with smooth surface attached to the proximal end of the femoral component. The femoral head component contains a deflated balloon. The hip hemiarthroplasty device has a first position and a second position. The first position occurs when the hip hemiarthroplasty device is rolled lengthwise into a slimmer form. The second position occurs when the deflated balloon has been inflated with a molding within the patient.

In an embodiment, the device includes an external sleeve containing a flexible rod to guide the hip hemiarthroplasty device into correct position within the patient. The external sleeve is adjacent to the femoral component In an embodiment, the device includes a insertion sleeve surrounding the deflated balloon. The device further includes a guiding string attached to the insertion sleeve. A force can be applied to the guiding string to guide the hip hemiarthroplasty device into the correct position within the patient. The device further includes a tab that can be pulled to detach the insertion sleeve from the device, so the insertion sleeve can be removed from the patient.

In an embodiment, the device further comprises a trajectory guidance tube adjacent to the device to guide the femoral component down the reamed femoral canal.

In an embodiment, the femoral component and the femoral head component include radioopaque markers to indicate positioning within the patient.

These and other important Objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Certain embodiments of the current invention can be used in lieu of hip hemiarthroplasty and/or hip pinning in a sedentary or household-ambulating patient who has a hip fracture. The advantages of the device are immediate fixation of the fracture, immediate weight bearing after surgery, and reduced invasiveness compared to a hip hemiarthroplasty. Hip hemiarthroplasty is performed more commonly for hip fractures than hip pinning because pinning requires a stable fracture pattern.

Preparing the Patient

Figure 1:
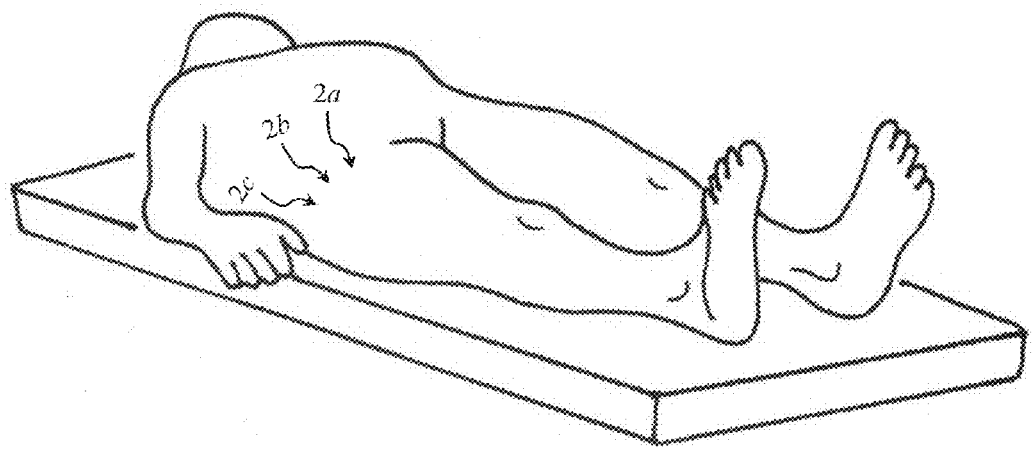
FIG. 1 depicts an illustration of a subject in a supine position with common portals (i.e., anterior, anterolateral, lateral) for hip arthroscopy.
Figure 2:
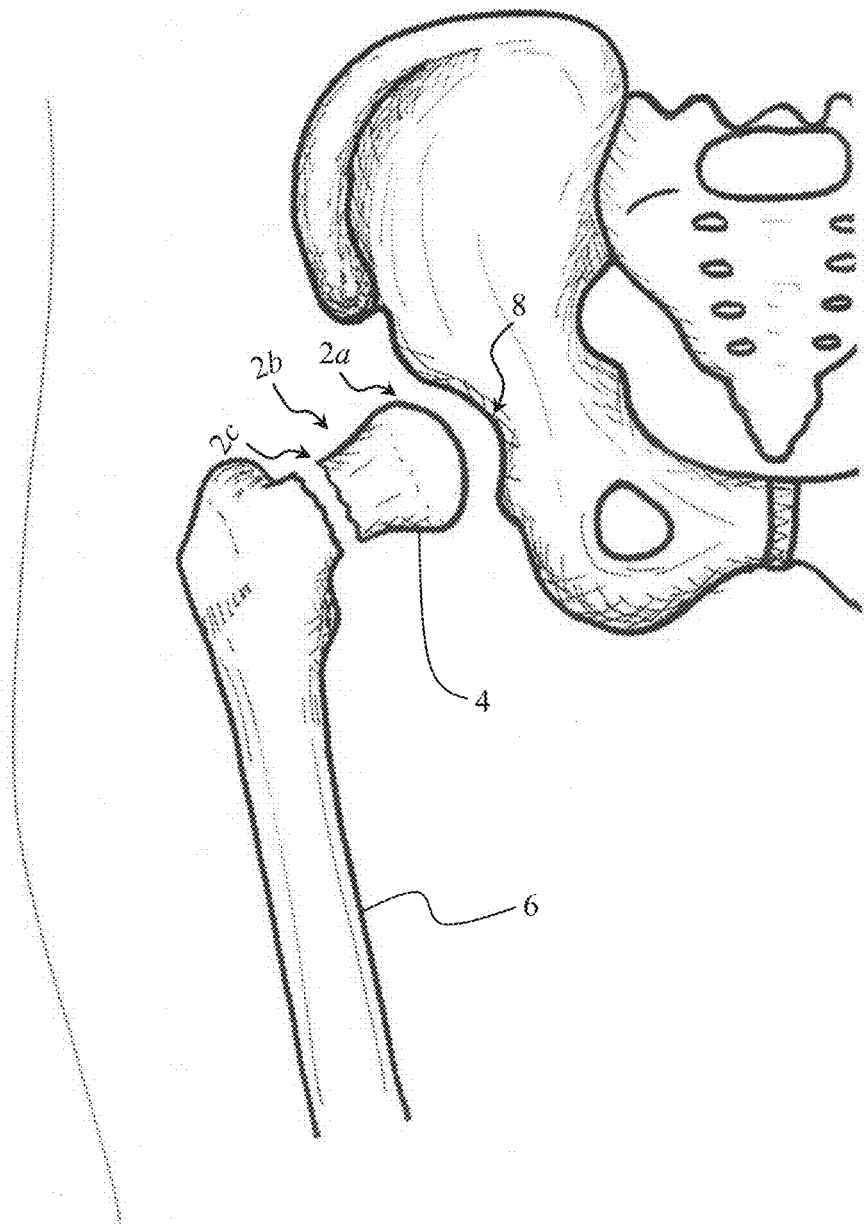
FIG. 2 depicts common portals (i.e., anterior, anterolateral, lateral) for hip arthroscopy.

A patient is positioned supine on an operating table. The operative leg can be internally rotated by about 15° to compensate for normal hip anteversion, such that the surgeon can orient instruments parallel to the operating room floor, ceiling, operating table, or other landmark to achieve correct orientation to the femoral neck. Using fluoroscopy, the hip landmarks can be established on the patient's skin. As depicted in FIGS. 1 and 2, common hip arthroscopic portals include anterior portal 2a, anterolateral portal 2b, and lateral portal 2c. Once the desired portal 2a, 2b, 2c has been established within the patient, the hip capsule can be irrigated to remove hematoma from the capsule.

Fractured femoral head 4 is then removed. Femoral head 4 can be removed using common arthroscopic instruments, for example camera, grasper, and bone burr, to remove the femoral head fragments. Additional portals may be required to effectively immobilize femoral head 4 so that the burr may be used effectively.

Accessing the Operative Femur

Figure 3:
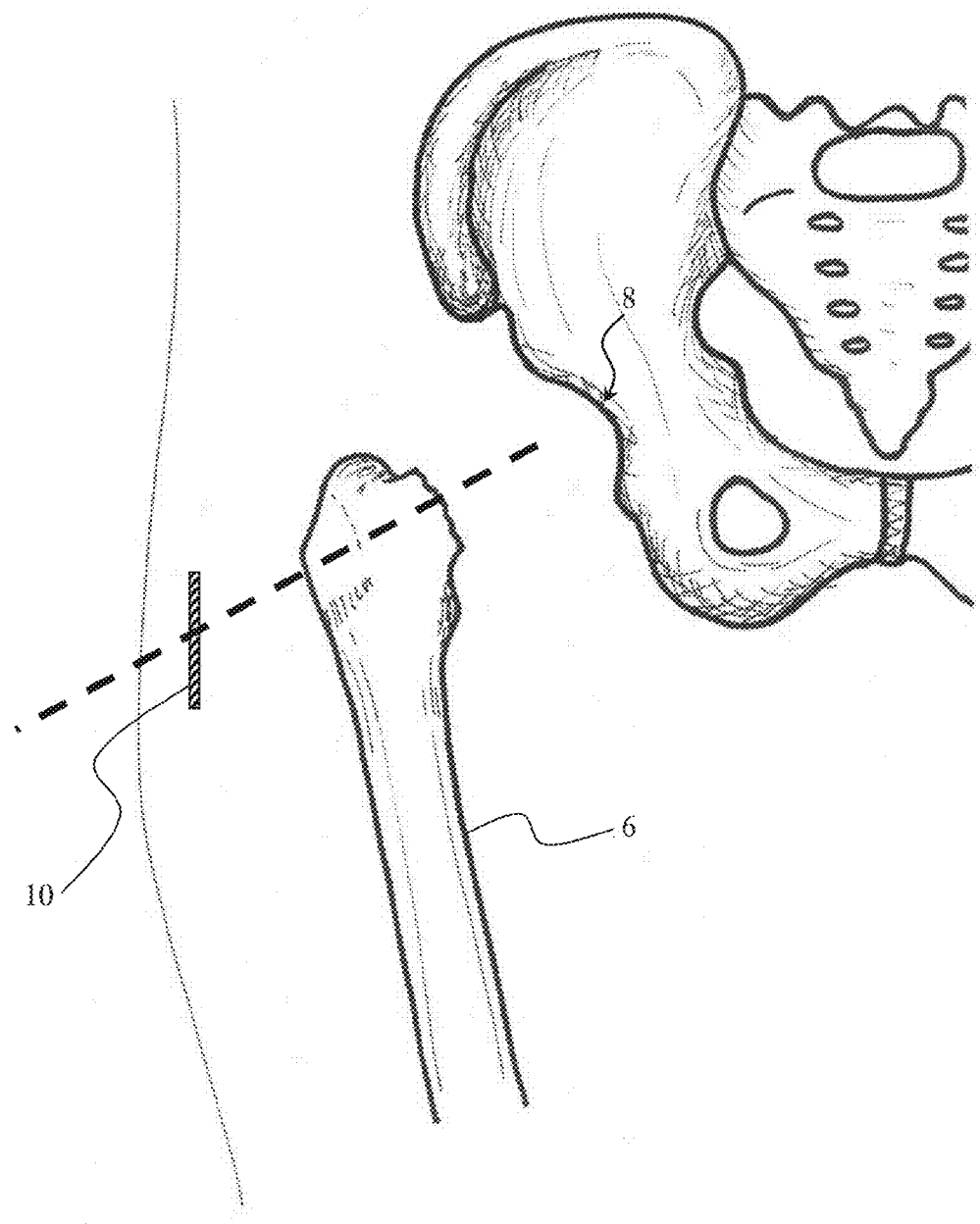
FIG. 3 depicts a hip fracture with removed femoral head and a lateral thigh incision.

Once femoral head 4 is removed and the fractured surface of the femoral neck has been irrigated and smoothed, incision 10 on the lateral aspect of the thigh is made as shown in FIG. 3. Incision 10 is positioned so that it is coincident to a line drawn through the path of the femoral neck. Dissection of the soft tissues is taken down to the lateral aspect of the greater trochanter.

Figure 4:
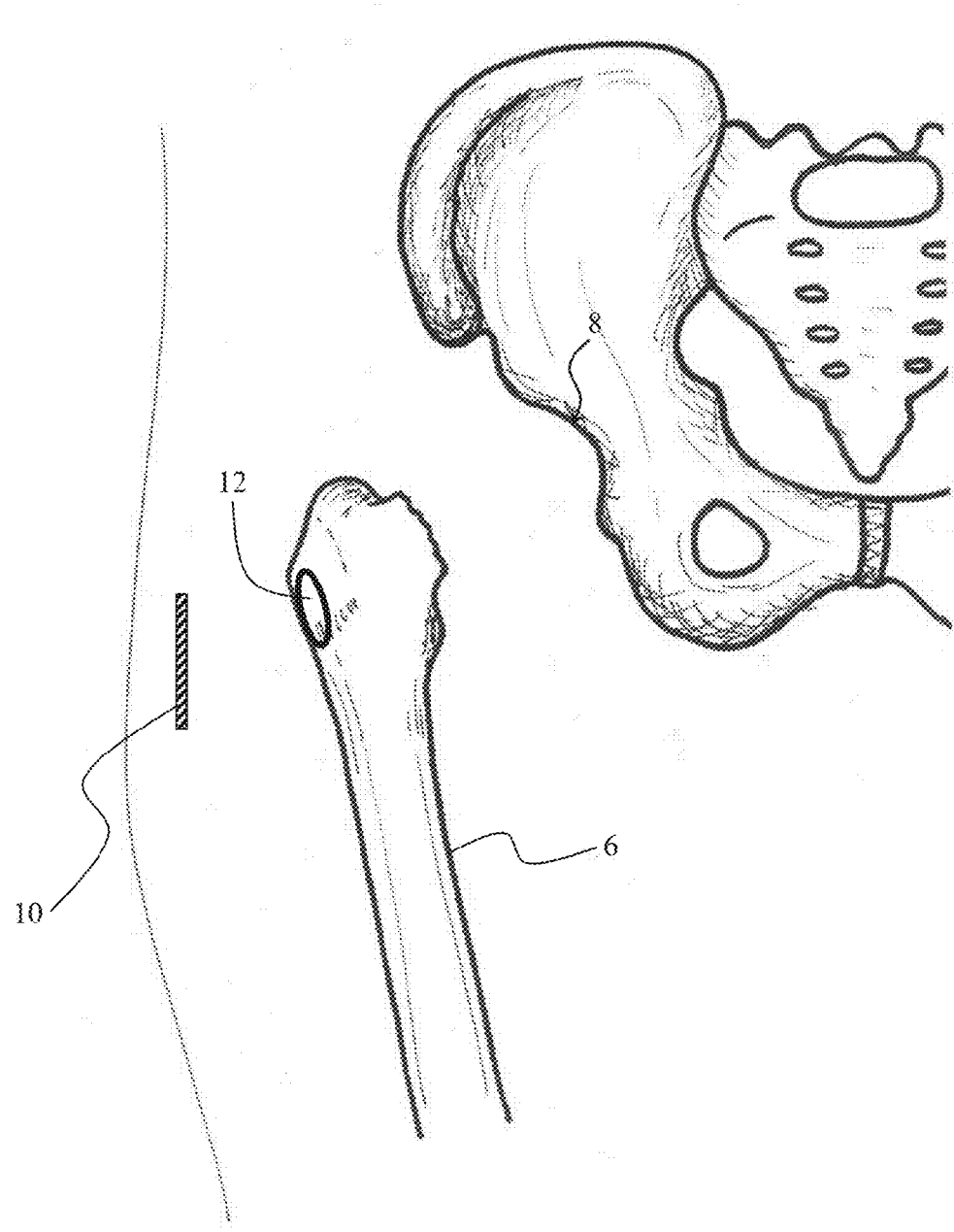
FIG. 4 depicts a lateral thigh incision and a lateral trochanteric osteomy hole within the cortex of a femoral neck.

As shown in FIG. 4, lateral trochanteric osteomy hole 12 is created in the cortex of the lateral femur by conventional instruments, for example a drill bit through incision 10. The size of hole 12 varies with the size of the patient; however, hole 12 would typically range from about 15 mm to about 20 mm in diameter.

Reaming the Femoral Canal

Figure 5:
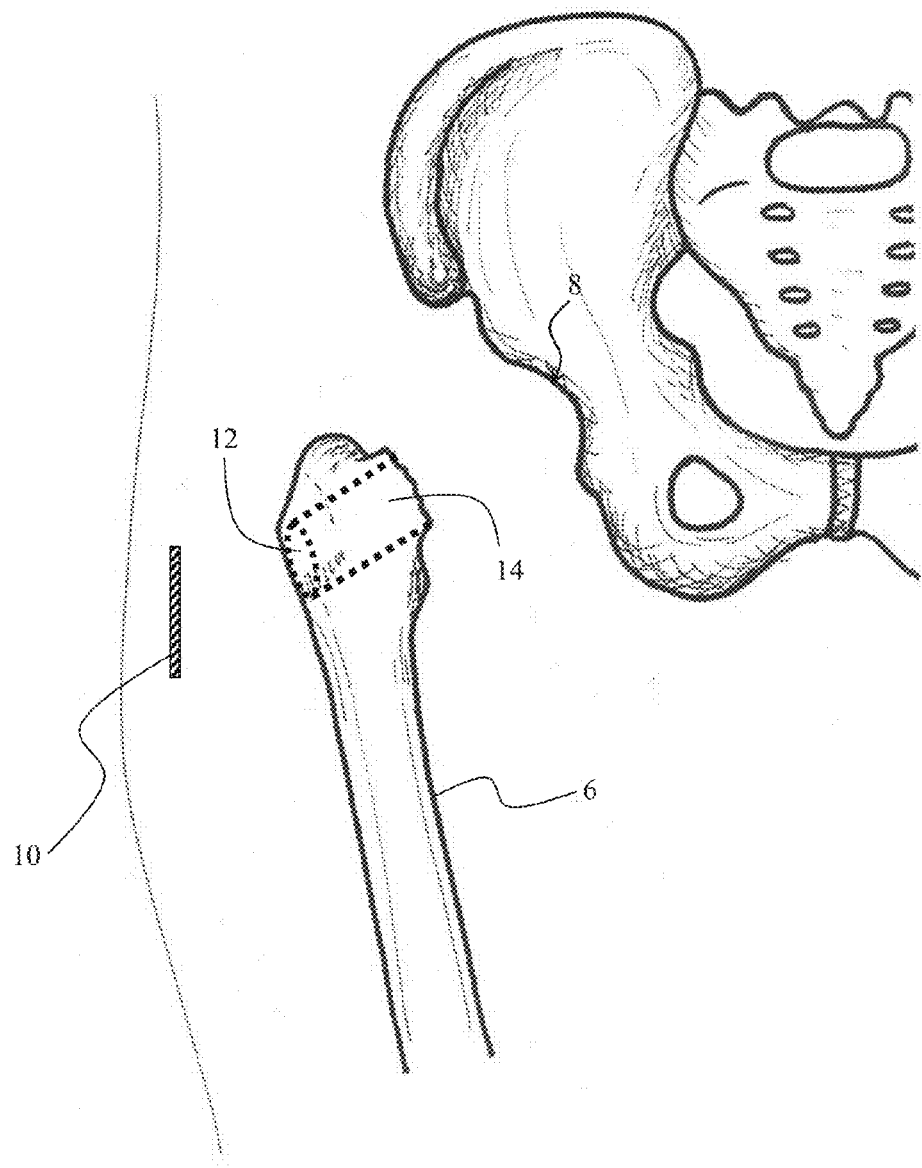
FIG. 5 depicts a lateral thigh incision, a lateral trochanteric osteomy, and a reamed femoral neck.

As shown in FIG. 5, canal-finding reamer (not shown) of similar diameter to hole 12 is then used to extend hole 12 into the cortex through the femoral neck to create reamed femoral neck 14. Canal-finding reamers are commercially available from many orthopedic companies.

Figure 6:
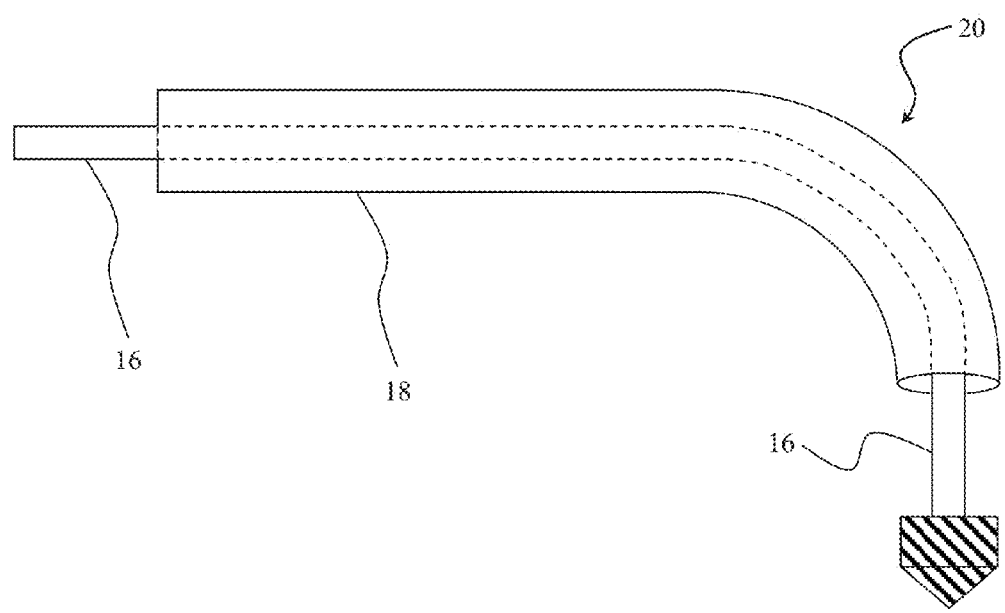
FIG. 6 depicts a flexible reamer inside of a trajectory guidance tube with 90° elbow to direct the reamer down the femoral shaft.
Figure 7:
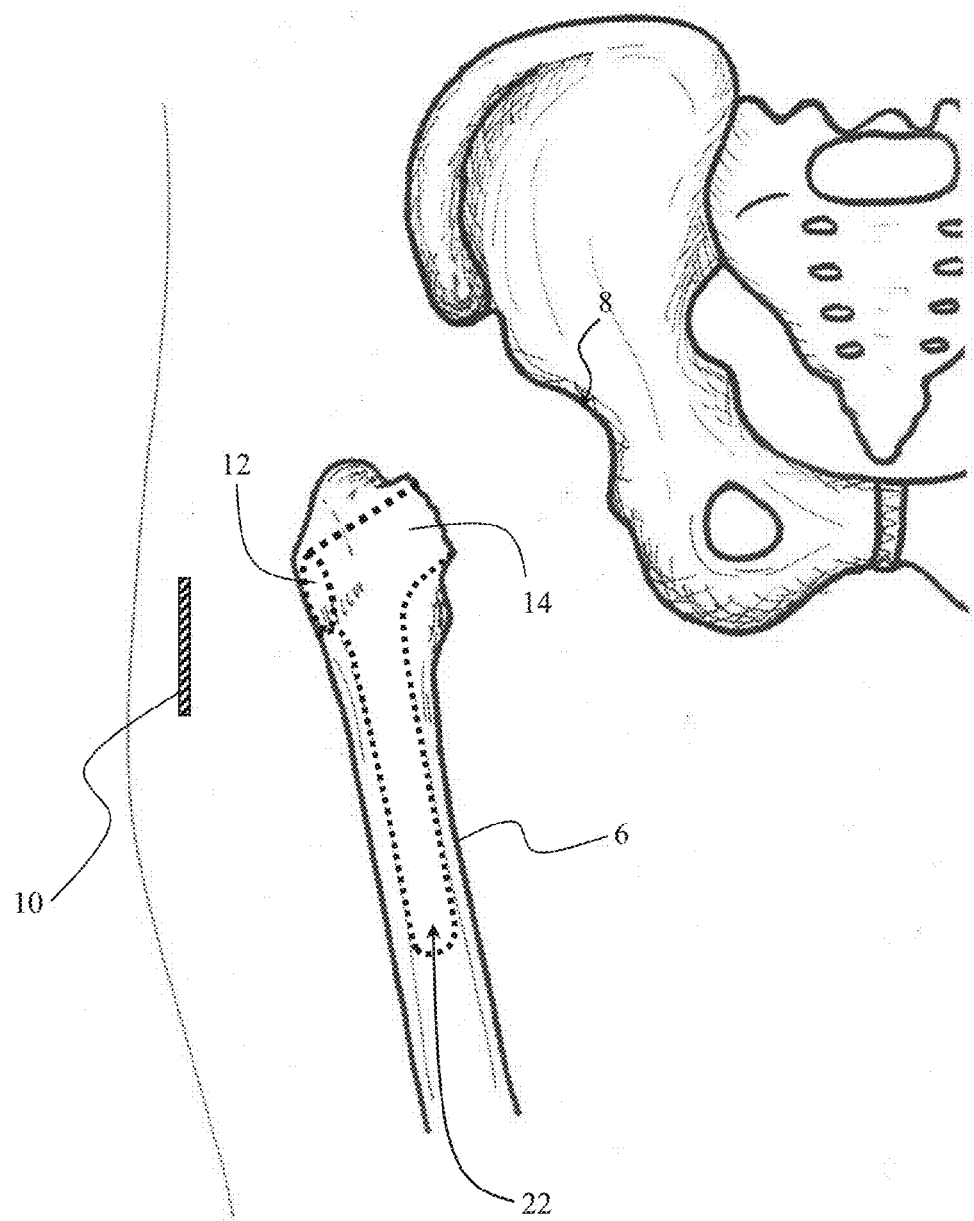
FIG. 7 depicts depicts a lateral thigh incision, a lateral trochanteric osteomy, a reamed femoral neck and a reamed femoral canal.

As shown in FIG. 6, reaming of the femoral canal is undertaken using highly flexible-shaft reamers 16 and guide tube 18 with 90° elbow 20. Guide tube 18 is used to direct flexible-shaft reamers 16 down femoral canal 22. Flexible-shaft reamers are commercially available from many orthopedic companies. Reamers 16 may be marked to allow reaming to the proper depth. Reaming depth and trajectory can be checked with fluoroscopy, as depicted in FIG. 7. The use of reamer 16 in this manner may be enhanced in patients with low bone density (e.g., osteopenia or osteoporosis) with the use of flexible tube 34 that would traverse guide tube 18 with 90° elbow 20. Flexible tube 34 can have an outer diameter slightly smaller than the inner diameter of guide tube 18. Flexible tube 34 can have an inner diameter slightly larger than the outer diameter of reamer 116. Flexible tube 34 would be advanced behind reamer 16 to prevent deviation of the course of reamer 16 outside of the bone. Flexible tube 34 could be made of any biocompatible, flexible synthetic materials, individually or in combination.

When reamer 16 has completed reaming femoral canal 22, as depicted in FIG. 7, the entire wound can be irrigated with a commercially available pulse-lavage device (e.g., STRYKER ORTHOPAEDICS).

Inserting the Hip Prosthesis

Figure 8:
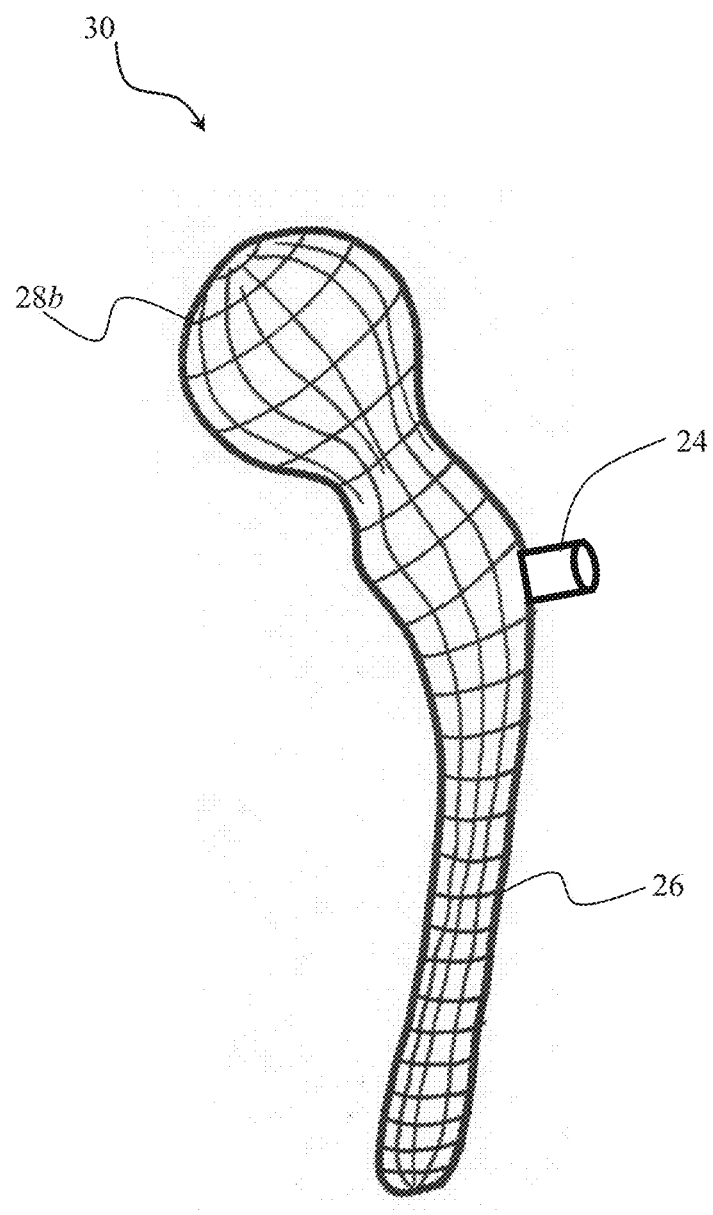
FIG. 8 depicts a femoral component after inflation with bone cement, the femoral component superficially resembling a typical hemiarthroplasty component.

Next, a hip prosthesis, denoted generally by the reference numeral 30, is introduced into the wound. Hip prosthesis 30 includes femoral component 26 and femoral head component 28. Femoral head component 28 includes deflated balloon 28a, which, when inflated with a molding, for example bone cement (polymethylmethacrylate), would take the form of hip hemiarthroplasty component 28b, as shown in FIG. 8.

Hip prosthesis 30 could take the form of several embodiments, all of which would be made with a liner that includes a flexible material that resists stretching. Many materials have this property; examples include fiberglass and carbon fiber. Femoral head component 28 is surfaced with a smooth material to allow low-friction articulation with acetabulum 8.

Hip prosthesis 30 can be manufactured with radioopaque markers to indicate the most proximal and distal aspects of hip prosthesis 30 so that position of femoral component 26 and deflated femoral head component 28a may be checked prior to inflation with molding. Other radioopaque markers could be used as necessary to facilitate positioning of hip prosthesis 30. A marker at the base of femoral neck 14 could be one such marker.

Deflated femoral head component 28a may be inflated with air or water prior to injection of molding in order to visualize femoral head component 28 in its inflated state to ascertain positioning. An additional embodiment of hip prosthesis 30 includes inflating deflated femoral head component 28a with water or air prior to cementation to incorporate small fenestrations (typically 2-3 mm diameter) along femoral component 26. The small fenestrations would allow molding to escape the device and interdigitate with the patient's bone, which is the normal mode by which molding, such as bone cement, achieves fixation.

Figure 9:
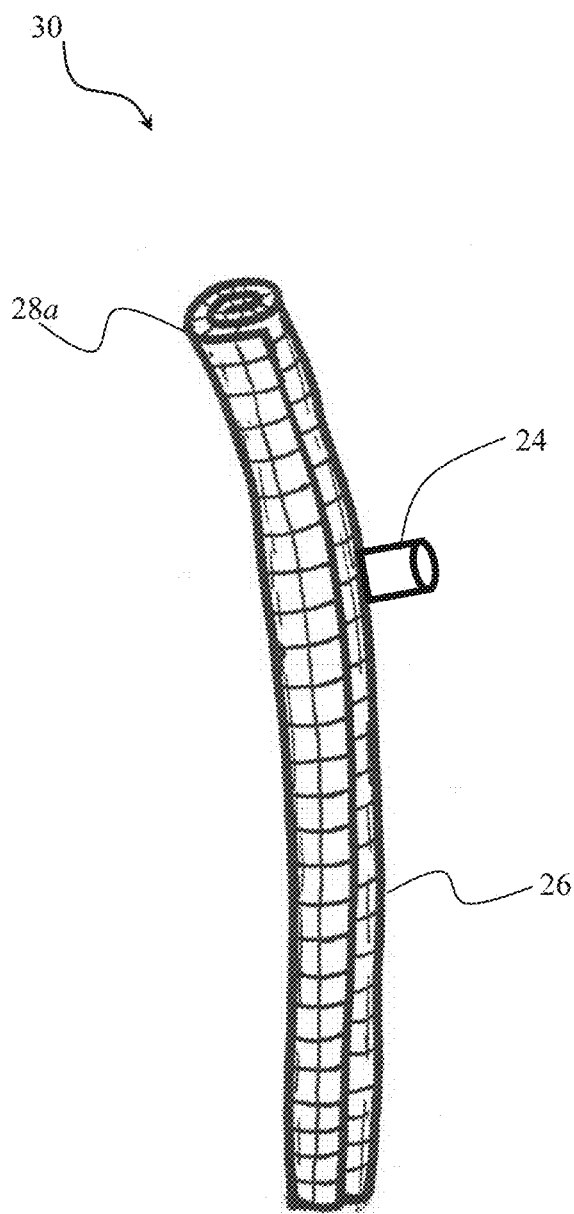
FIG. 9 depicts a femoral component and femoral head component rolled lengthwise to facilitate insertion into a subject, the femoral component having an inlet for cement injection.

Insertion of the distal portion of femoral component 26 into femoral canal 22 of the patient can be performed in several ways. An embodiment, as depicted in FIG. 9, involves femoral component 26 and femoral head component 28a initially rolled lengthwise into a slimmer form to facilitate insertion into the patient.

Figure 10:
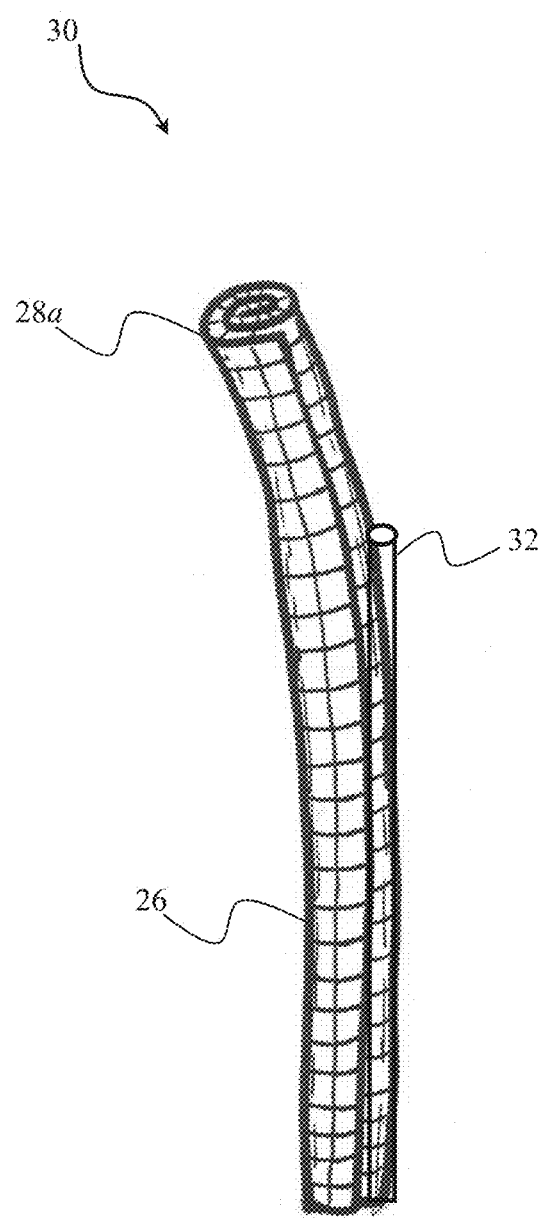
FIG. 10 depicts a femoral component and femoral head component rolled lengthwise to facilitate insertion into a subject, the femoral component having a collapsible external sleeve along the femoral shaft portion of the component to allow positioning within the intramedullary canal.
Figure 11:
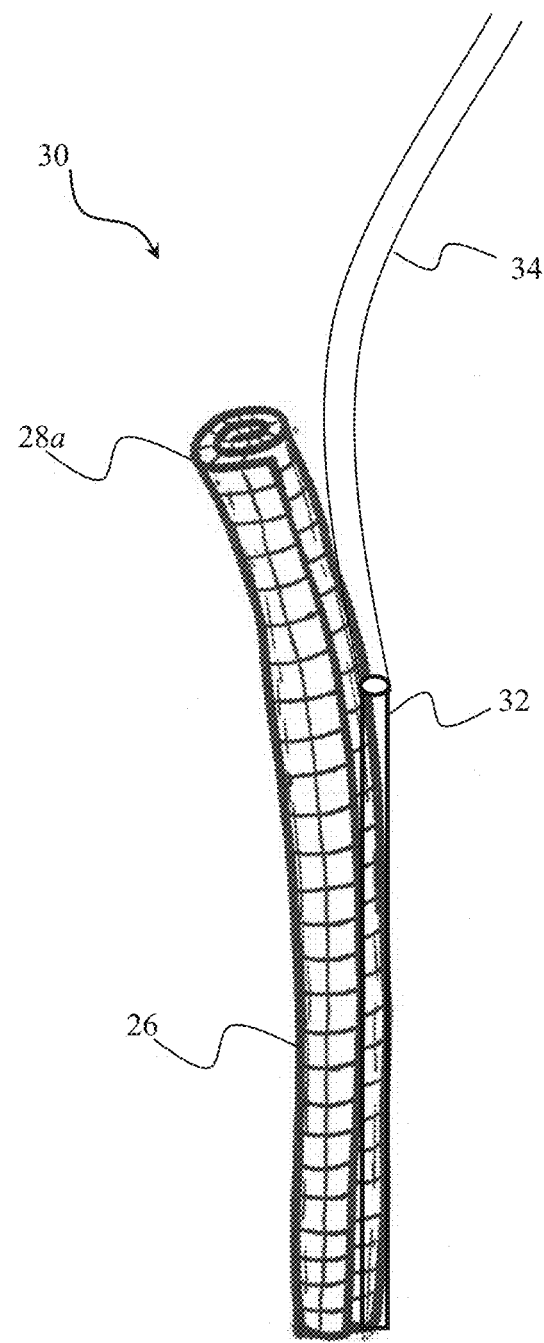
FIG. 11 depicts a femoral component and femoral head component rolled lengthwise to facilitate insertion into a subject, the femoral component having a collapsible external sleeve along the femoral shaft portion of the component and a flexible insertion rod placed in the external sleeve.
Figure 12:
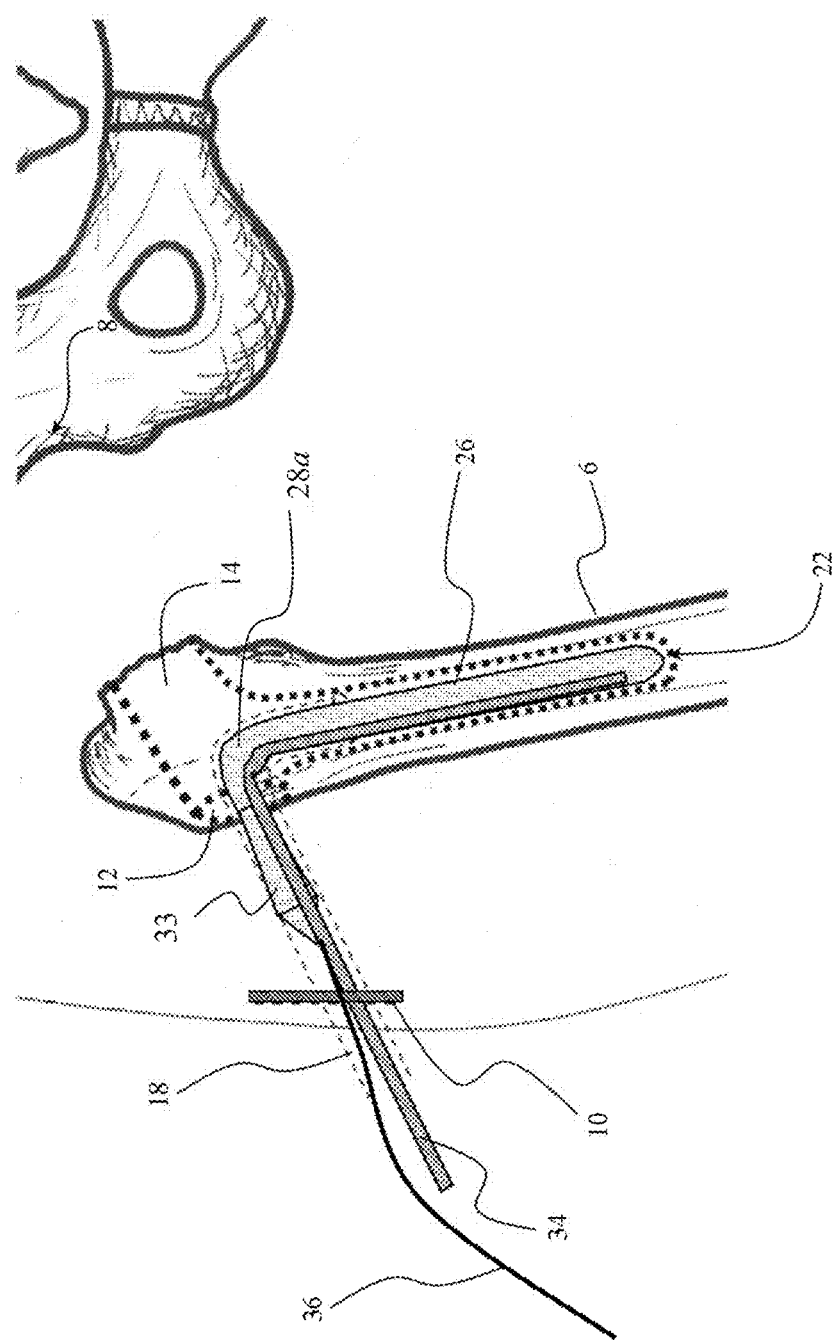
FIG. 12 depicts a femoral component having an insertion sleeve with narrow base and attached guiding string to allow positioning in the acetabulum of a subject.

External sleeve 32 on the outside of femoral component 26 allows for placement of flexible tube 34 to be inserted down femoral canal 22 adjacent to femoral component 26, as shown in FIGS. 10-12. This positioning is aided by use of guide tube 18 previously used for trajectory guidance of flexible reamers 16 with 90° elbow 20, as shown in FIG. 12. External sleeve 32 can be collapsible so that when molding is introduced into femoral canal 22, external sleeve 32 will not prevent complete inflation of femoral component 26 with molding.

Figure 13:
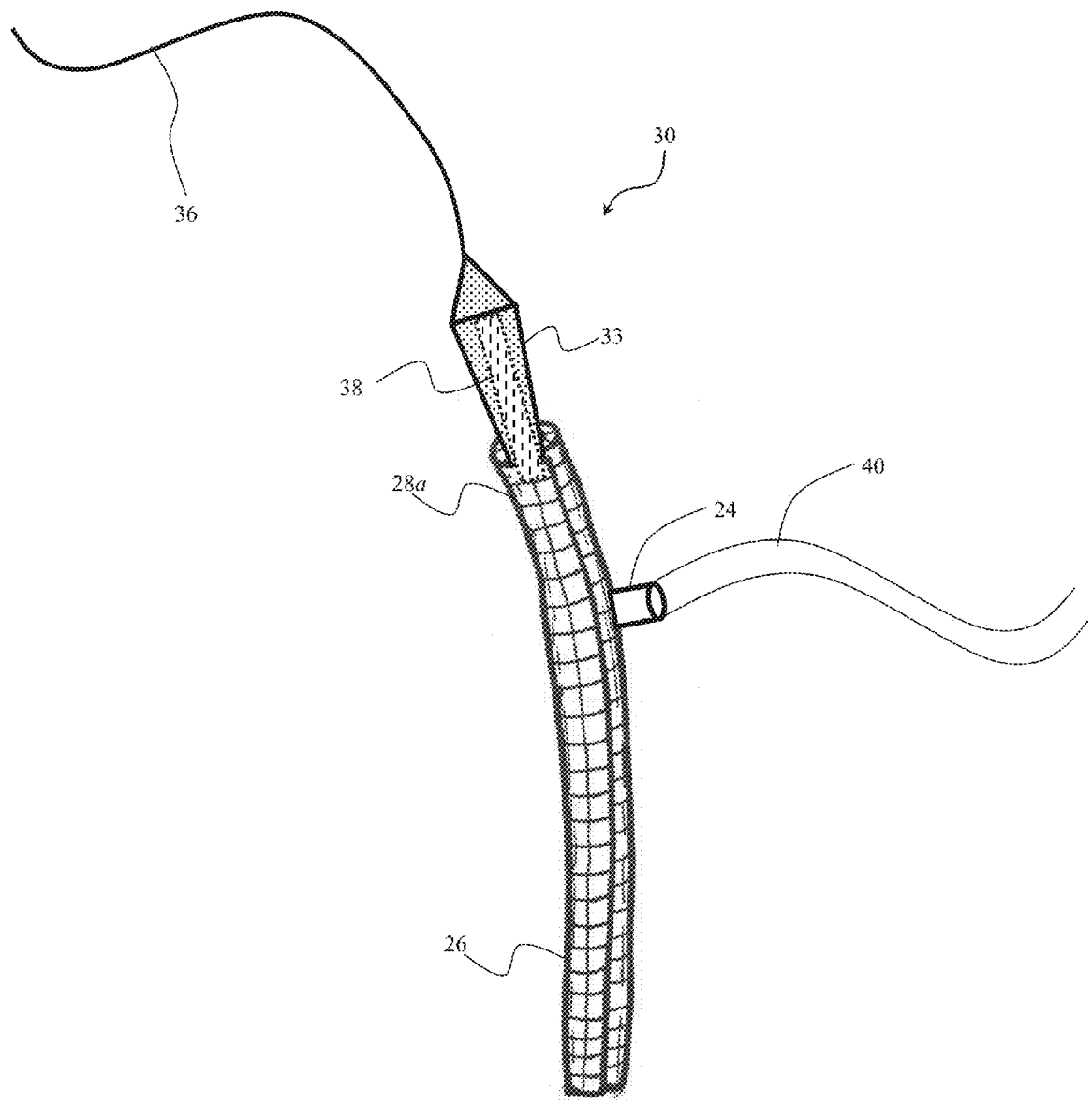
FIG. 13 depicts an illustration of a femoral component inserted into a femoral canal of a subject, the femoral component having a flexible rod inserted into an external sleeve, a trajectory guidance tube with 90° elbow, and guiding string for positioning of femoral head component in the acetabulum of the subject.

Femoral head portion 28 of hip prosthesis 30 includes insertion sleeve 33 over the top portion of deflated femoral head component 28a when in its rolled-up form, as shown in FIGS. 12 and 13. Insertion sleeve 33 has string 36 attached to the end of sleeve 33 at a proximal aspect of femoral head component 28. Sleeve 33 can be manufactured so that its diameter about femoral neck 14 is smaller than the diameter of deflated femoral head component 28a, thereby allowing sleeve 33 to be pulled with substantial force, in turn allowing sleeve 33 and femoral head component 28a to be introduced into acetabulum 8.

Figure 14:
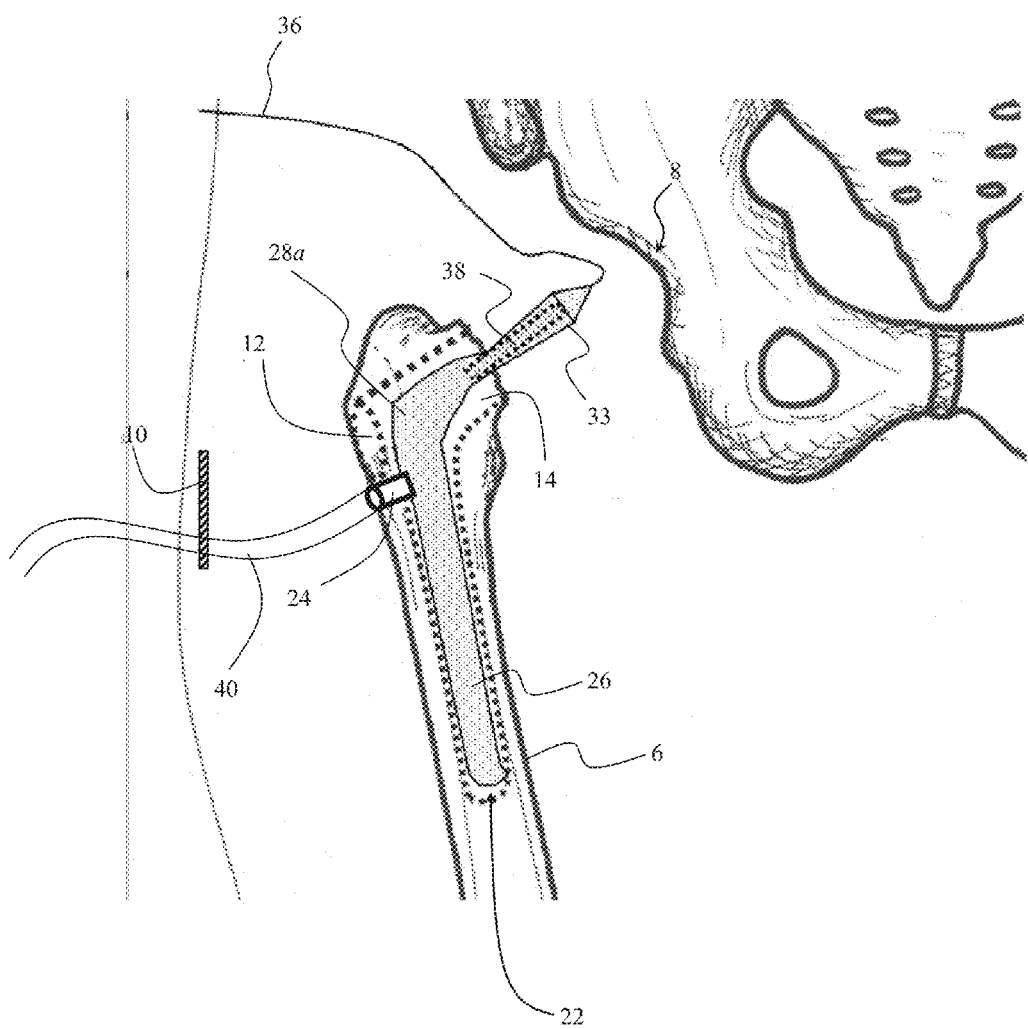
FIG. 14 depicts a femoral head component located in the acetabulum of a subject after a guiding string has been pulled through an arthroscopic portal.

After insertion of the distal portion of femoral component 26 into femoral canal 22, string 36 can be passed through lateral thigh incision 10 into acetabulum 8 where string 36 can be visualized with an arthroscope. A grasper (not shown) inserted into one of the arthroscopic portals 2a, 2b, 2c can then be used to pull string 36 through the portal 2a, 2b, 2c and bring insertion sleeve 33 containing the femoral head component 28a into acetabulum 8, as shown in FIG. 14.

Insertion sleeve 33 can be manufactured to include tab 38 on sleeve 33. Tab 38 can be pulled by an arthroscopic grasper (not shown) through arthroscopic portal 2a, 2b, 2c after introduction of the deflated femoral head component 28a into acetabulum 8, as shown in FIG. 13. This releases the narrow base of sleeve 33 over the femoral head component 28a and allows sleeve 33 to be pulled through arthroscopic portal 2a, 2b, 2c with attached string 36 and removed from the body.

Figure 15:
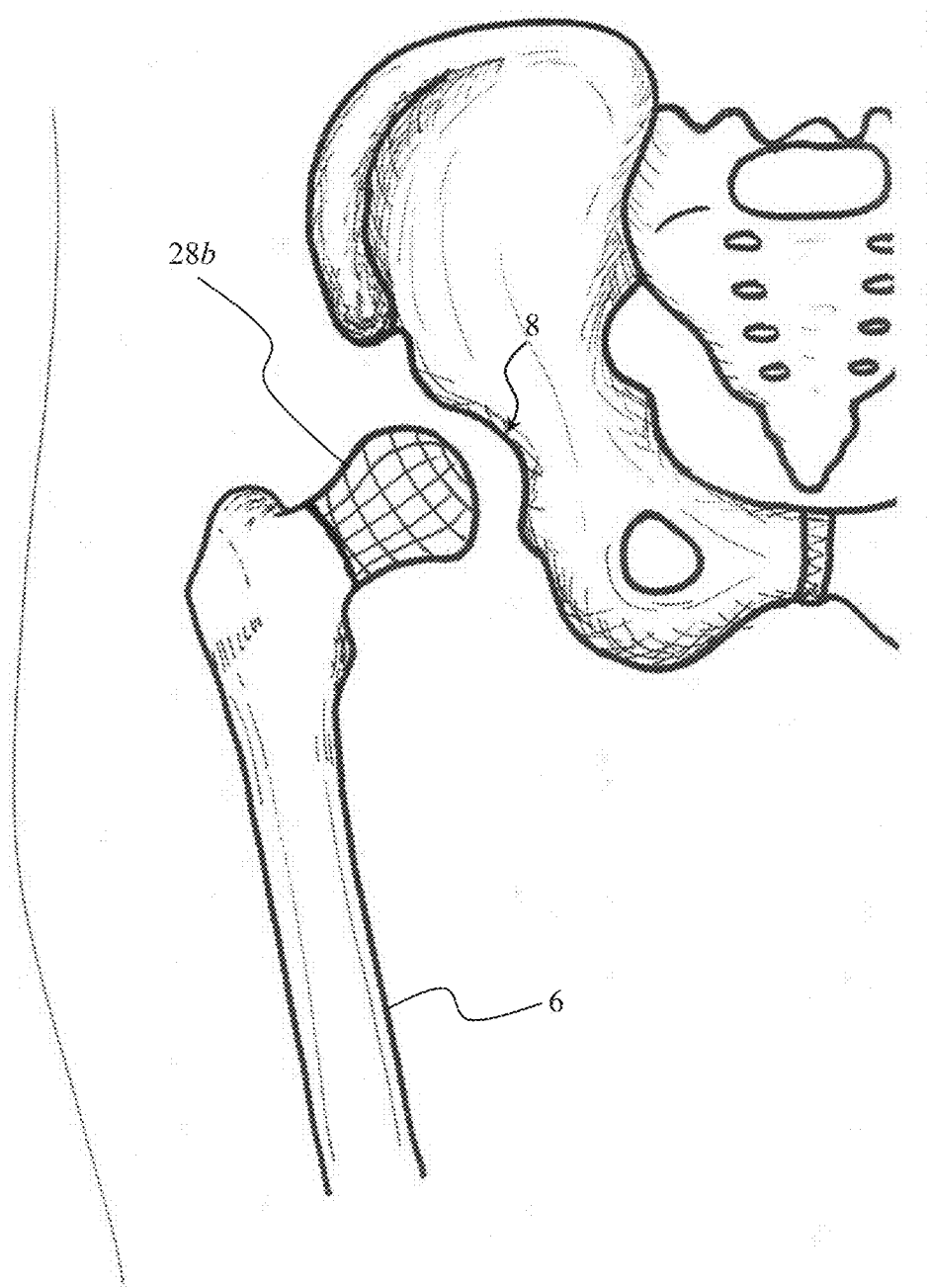
FIG. 15 depicts a resultant femoral head component upon inflation with molding within a subject and relative to the acetabulum of the subject.

Positioning of femoral component 26 and deflated femoral head component 28a can be confirmed with fluoroscopy. Deflated femoral head component 28a may then be injected with molding, resulting in inflated femoral head component 28b, as depicted in FIG. 15.

The indications and candidates for this procedure include non-ambulatory patients with hip fracture or patients with limited ambulatory capacity and hip fracture. This procedure would be less invasive than hip hemiarthroplasty. This procedure provides better pain relief than hip pinning, which requires a significant amount of healing prior to pain relief. Better pain relief would allow patients to begin transfers in position sooner than with hip pinning. Early ambulation after hip fracture is known to decrease complications such as deep venous thrombosis and pulmonary emboli.

Benefits of this procedure when compared to hip pinning are that patients would have pain relief similar to that experienced with a hemiarthroplasty without the protracted healing period required with hip pinning.

Benefits of this procedure when compared to hip hemiarthroplasty are that it is less invasive, and there is no violation of hip capsule with significantly less risk of hip dislocation. This feature would be especially beneficial in patients with dementia and neuromuscular disorders that dispose to dislocation.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A surgical technique for complete replacement of a femoral head in a subject or replacement of an articular surface of the femoral head in the subject, the technique comprising the steps of:
    positioning the subject with a fractured hip in a position suitable for the surgical technique, the fractured hip including the femoral head and a femoral neck;
    removing the femoral head from the subject;
    accessing the femoral neck and a femoral canal of an operative femur;
    reaming the femoral neck and the femoral canal of the operative femur;
    inserting a hip prosthesis into a wound formed from reaming the femoral canal, the hip prosthesis containing a femoral component disposed within the reamed femoral canal and a deflated balloon disposed within an acetabulum of the subject, the hip prosthesis having a deflated position when collapsed into a compact position suitable for insertion into the reamed femoral canal, the femoral component expandable to fill the spatial confines of the reamed femoral canal; and
    injecting a molding into the hip prosthesis to form an inflated position, such that the deflated balloon becomes inflated to expand within the reamed femoral neck and to form an inflated balloon that resembles the femoral head of the subject, such that the inflated balloon can completely replace the femoral head of the subject.

2. The surgical technique of claim 1, wherein the step of accessing the femoral neck and the femoral canal of the operative femur of the subject includes:
    making an incision on the subject on a lateral aspect of an operative thigh of the subject, whereby the incision is coincident to a line drawing through a path of the femoral neck; and
    drilling a hole into a cortex of the femoral neck of the subject trough the incision.

3. The surgical technique of claim 2, wherein the drilled hole is about 15 mm in diameter to about 20 mm in diameter.

4. The surgical technique of claim 2, wherein the step of reaming the femoral neck and the femoral canal of the operative femur includes inserting a reamer through the drilled hole, wherein the reamer has a flexible shaft, the reamer being disposed within a lumen of a trajectory guidance tube.

5. The surgical technique of claim 4, wherein the trajectory guidance tube contains a 90° elbow to direct the reamer down the length of the femoral canal.

6. The surgical technique of claim 1, wherein the position is a supine position, the supine position further comprising internally rotating the operative leg of the subject by about 15°, whereby a surgeon can orient surgical instruments parallel to a landmark to achieve correct orientation to the femoral neck.

7. The surgical technique of claim 1, wherein the step of removing the femoral head from the subject is performed using one or more instruments selected from the group consisting of a camera, a grasper, and a bone burr.

8. The surgical technique of claim 1, wherein the molding is bone cement.

9. The surgical technique of claim 1, further comprising the step of inflating the deflated balloon with water or air prior to the step of inflating the deflated balloon with the molding.

10. The surgical technique of claim 1, wherein the hip prosthesis further includes an external sleeve attached to a flexible rod to guide the femoral component within the reamed femoral canal of the subject, the external sleeve being adjacent to the femoral component.

11. The surgical technique of claim 10, wherein the external sleeve is collapsible.

12. The surgical technique of claim 1, wherein the hip prosthesis further includes an insertion sleeve surrounding the deflated balloon.

13. The surgical technique of claim 12, wherein the hip prosthesis further includes a guiding string attached to the insertion sleeve, a force applied to the guiding string to guide the femoral head component within the acetabulum of the subject.

14. The surgical technique of claim 12, wherein the insertion sleeve includes a tab that is pulled to detach the insertion sleeve from the hip prosthesis, whereby the insertion sleeve can be removed from the subject.

15. The surgical technique of claim 1, further comprising the step of rolling the hip prosthesis lengthwise into a slimmer form to form the deflated position prior to the step of inserting the hip prosthesis into the wound.

16. The surgical technique of claim 1, further comprising the step of monitoring the surgical technique with fluoroscopy while the surgical technique is being performed.

17. A surgical technique for minimally invasive replacement of a fractured femoral head in hip arthroscopy, the technique comprising the steps of:
positioning a subject with a fractured hip, containing the fractured femoral head and a femoral neck, in a supine position suitable with an operative leg of the subject internally rotated by about 15°, whereby a surgeon can orient surgical instruments parallel to a landmark to achieve correct orientation to the femoral neck;
removing the fractured femoral head from the subject through use of conventional instruments selected from the group consisting of a camera, a grasper, and a bone burr;
making an incision on a lateral aspect of an operative thigh of the subject, such that the incision is coincident to a line drawing through a path of the femoral neck;
drilling a hole into a cortex of the femoral neck of the subject through the incision, wherein the hole is about 15 mm in diameter to about 20 mm in diameter;
reaming the femoral neck and a femoral canal of the operative femur by inserting a reamer through the drilled hole, wherein the reamer has a flexible shaft, the reamer being disposed within a lumen of a trajectory guidance tube containing a 90° elbow;
irrigating the region of the fractured hip with a pulse-lavage device;
rolling a hip prosthesis lengthwise into a slimmer form, the hip prosthesis containing
a deflated balloon with a smooth surface,
an insertion sleeve surrounding the deflated balloon,
a femoral component inserted into the femoral canal of the subject,
a collapsible external sleeve containing a flexible rod to guide the femoral component within the reamed femoral canal of the subject, wherein the external sleeve is adjacent to the femoral component,
a guiding string attached to the insertion sleeve, the guiding string pulled by the surgeon to guide the femoral head component within the acetabulum of the subject, and
a tab that is pulled to detach the insertion sleeve from the hip prosthesis, whereby the insertion sleeve can be removed from the subject;
inserting the hip prosthesis into a wound formed from reaming the femoral canal, where the hip prosthesis is inserted through the wound through the incision by inserting the distal end of the femoral component first, the femoral component disposed within the reamed femoral canal and the deflated balloon disposed within the acetabulum of the subject;
inflating the hip prosthesis with water or air; and
injecting bone cement into the hip prosthesis, such that the deflated balloon becomes inflated and becomes a neo-femoral head.

* * * * *